United States Patent

Cereda et al.

(10) Patent No.: US 6,586,435 B2
(45) Date of Patent: Jul. 1, 2003

(54) BENZIMIDAZOLONE DERIVATIVES DISPLAYING AFFINITY AT THE SEROTONIN AND DOPAMINE RECEPTORS

(75) Inventors: Enzo Cereda, Novi Ligure (IT); Luciano Maiocchi, Cernobbio (IT); Alessandro Brambilla, Milan (IT); Ettore Giraldo, Milan (IT); Giovanni Battista Schiavi, Asola (IT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/933,609

(22) Filed: Aug. 21, 2001

(65) Prior Publication Data

US 2002/0103208 A1 Aug. 1, 2002

Related U.S. Application Data

(60) Provisional application No. 60/250,664, filed on Dec. 1, 2000.

(30) Foreign Application Priority Data

Sep. 19, 2000 (EP) .............................. 00830625

(51) Int. Cl.$^7$ .................. A61K 31/496; A61K 31/4439; A61K 31/506; A61P 25/24; A61P 25/18
(52) U.S. Cl. .................. 514/252.19; 544/333; 544/295; 544/370; 546/16; 546/87; 546/199; 514/278; 514/292; 514/254.06; 514/326
(58) Field of Search .............................. 544/370, 295, 544/333; 514/254.06, 252.19, 326, 292, 278; 546/199, 87, 16

(56) References Cited

U.S. PATENT DOCUMENTS 5,576,318 A * 11/1996 Bietti et al. .................. 514/253

FOREIGN PATENT DOCUMENTS

| EP | 0 526 434 A1 | 2/1993 |
| EP | 0 705 832 A1 | 4/1996 |
| WO | WO 95 34555 A1 | 12/1995 |

OTHER PUBLICATIONS

Chalmers (TiPS vol. 17, pp. 166–172 Apr. 1996).*
Lyrer (Schweiz. Med. Wochenschr., vol. 124, #45, 2005–2012 1994).*
Frampton (Drugs and Aging 7(6) 480–503 1995).*

* cited by examiner

Primary Examiner—Mark L. Berch
Assistant Examiner—Kahsay Habte
(74) Attorney, Agent, or Firm—Robert P. Raymond; Timothy X. Witkowski; Mary-Ellen Devlin

(57) ABSTRACT

Compound of formula (I)

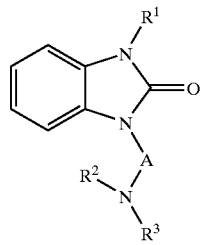

wherein:

$R^1$ is hydrogen or $C_1$–$C_6$-alkyl optionally substituted by $C_3$–$C_6$-cycloylalkyl;

$R^2$ and $R^3$ together with the nitrogen form a saturated or unsaturated 5- or 6-membered heterocyclic ring optionally containing nitrogen or oxygen as an additional heteroatom, wherein the heterocyclic ring thereof is substituted by a group selected from phenyl, benzyl, and diphenylmethyl, each optionally mono- or di-substituted by one or two groups selected from $CF_3$, $C_1$–$C_4$-alkyl, $C_1$–$C_4$-alkoxy, phenyl, benzyl, halogen, and OH, or $R^2$ and $R^3$ together with the nitrogen form a saturated or unsaturated 5- or 6-membered heterocyclic ring optionally containing nitrogen or oxygen as an additional heteroatom, the heterocyclic ring thereof linked via a single bond, a methylene-bridge, or spiro-connected to another saturated or unsaturated heterocyclic group containing one or two heteroatoms selected from oxygen and nitrogen, the heterocyclic group being optionally mono- or di-substituted by a group selected from $CF_3$, $C_1$–$C_4$-alkyl, $C_1$–$C_4$-alkoxy, phenyl, benzyl, halogen, =O, and OH, or $R^2$ and $R^3$ together with the nitrogen form a saturated or unsaturated bi- or tricyclic heterocyclic ring system optionally containing nitrogen or oxygen as an additional heteroatom, the heterocyclic ring system is optionally substituted by a group selected from $CF_3$, $C_1$–$C_4$-alkyl, $C_1$–$C_4$-alkoxy, phenyl, benzyl, halogen, =O, and OH; and A is $C_2$–$C_6$-alkenylene, their pharmaceutically acceptable salts, their preparation, and their use for therapeutic purposes.

8 Claims, No Drawings

BENZIMIDAZOLONE DERIVATIVES DISPLAYING AFFINITY AT THE SEROTONIN AND DOPAMINE RECEPTORS

RELATED APPLICATIONS

Benefit under 35 U.S.C. §119(e) of prior U.S. provisional application Serial No. 60/250,664, filed Dec. 1, 2000, is hereby claimed.

FIELD OF THE INVENTION

The present invention relates to novel pharmacologically active N,N'-disubstituted benzimidazolone derivatives and their addition salts which bind the serotonin or dopamine receptors, to their preparation and their use for therapeutic purposes. These compounds are able to discriminate the different serotonin and dopamine receptor subtypes like 5-$HT_{1A}$, 5-$HT_{2A}$, and $D_4$ at which they can act as agonists or antagonists. Owing to this pharmacological activity, the present compounds are useful in the treatment of anxiety disorders, affective disorders such as depression, psychosis and schizophrenia, eating disorders, sexual disorders, Parkinson, stroke and traumatic brain injury.

BACKGROUND OF THE INVENTION

Serotonin (5-HT) and dopamine (DA) recognize several well defined cell surface receptor subtypes. Among these, 5-$HT_{1A}$ and 5-$HT_{2A}$ having a high and a low affinity for 5-HT, respectively, and $D_4$ at which DA has high affinity, have been implicated in many Central Nervous System (CNS) disorders.

In the previous art, several classes of compounds able to interfere with the neurotransmission at 5-HT or DA receptor subtypes are known. Particularly, derivatives based on the core structure of the aryl piperazine and benzimidazolone have been described (e.g., GB 2023594; U.S. Pat. No. 3,472,854; U.S. Pat. No. 4,954,503; WO-9616949; WO-9501965; and WO-9833784), and targeted both to generic 5-HT or DA receptors and to a specific receptor subtype. In another patent (U.S. Pat. No. 5,576,318) are described compounds based both on the benzimidazolone and phenylpiperazine structures: in this latter case the described affinities are limited to 5-$HT_{1A}$ and 5-$HT_{2A}$ receptor subtypes.

DETAILED DESCRIPTION OF THE INVENTION

Now we describe, and this is the object of the present invention, new derivatives of a benzimidazolone core structure. The N-substituents are simple alkyl chains whereas the N'-substituents are alkenyl spacers connecting the benzimidazolone scaffold to a large set of secondary amines bearing other diversity points. The compounds included in this invention possess an interesting affinity profile at the serotonin and dopamine receptor subtypes: indeed some of them have a high and preferential affinity at a given site (e.g., 5-$HT_{1A}$, 5-$HT_{2A}$, or $D_4$) whereas some others have a mixed affinity at the said receptors. Moreover a selected pool of compounds possesses an agonistic activity at the 5-$HT_{1A}$ receptor coupled with an antagonistic activity at the 5-$HT_{2A}$ receptor. Owing to their peculiar profile, the present compounds may play a role in the regulation of neurotransmission at the serotonin and/or the dopamine sites and thus may be of value in the treatment of those diseases where an altered functioning of neurosignal transmission is present. Examples of these disorders include anxiety, depression, schizophrenia, Parkinson, sleep, sexual and eating disorders, stroke and brain injury. Particularly the compounds included in the present invention can be of value in the treatment of depression according to the mounting evidence that 5-$HT_{1A}$ full agonists or high efficiency partial agonists are required for a robust antidepressant effect. In fact, electrophysiology studies suggest that repeated administration of a variety of antidepressant treatments facilitate 5-$HT_{1A}$ neurotransmission in the hippocampus, possibly through either an increased sensitivity of post-synaptic 5-$HT_{1A}$ receptors or a decreased sensitivity of 5-$HT_{1A}$ autoreceptors. Furthermore, there is some evidence from controlled clinical trials to support this suggestion. In addition to the compound's ability to block the 5-$HT_{2A}$ receptor is also of value: indeed, the stimulation of 5-$HT_{1A}$ and 5-$HT_{2A}$ receptors lead to opposite electrical events, inhibitory and excitatory, respectively. Thus only a concurrent activation of 5-$HT_{1A}$ coupled with antagonism at 5-$HT_{2A}$ receptors may completely and rapidly inhibit 5-HT post-synaptic cells, an important physiological event for antidepressant effect.

The present invention pertains to compounds of general formula (I)

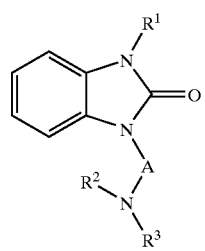

(I)

wherein $R^1$ denotes hydrogen or $C_1$–$C_6$-alkyl, being optionally substituted by $C_3$–$C_6$-cycloylalkyl;

$R^2$ and $R^3$ together with the nitrogen form a saturated or unsaturated 5- or 6-membered heterocyclic ring which may contain nitrogen or oxygen as an additional heteroatom, whilst the heterocyclic ring is substituted by a group selected from phenyl, benzyl, and diphenylmethyl, said group being optionally mono- or di-substituted by one or two groups selected from $CF_3$, $C_1$–$C_4$-alkyl, $C_1$–$C_4$-alkoxy, phenyl, benzyl, halogen, and OH, or $R^2$ and $R^3$ together with the nitrogen form a saturated or unsaturated 5- or 6-membered heterocyclic ring which may contain nitrogen or oxygen as an additional heteroatom, said heterocyclic ring being linked via a single bond, a methylene-bridge, or spiro-connected to another saturated or unsaturated heterocyclic group containing one or two heteroatoms selected from oxygen and nitrogen, said heterocyclic group being optionally mono- or di-substituted by a group selected from $CF_3$, $C_1$–$C_4$-alkyl, $C_1$–$C_4$-alkoxy, phenyl, benzyl, halogen, =O, and OH, or R² and R³ together with the nitrogen form a saturated or unsaturated bi- or tricyclic heterocyclic ring system which may contain nitrogen or oxygen as an additional heteroatom, said heterocyclic ring system being optionally substituted by a group selected from $CF_3$, $C_1$–$C_4$-alkyl, $C_1$–$C_4$-alkoxy, phenyl, benzyl, halogen, =O, and OH;

A $C_2$–$C_6$-alkenylene, preferably $C_2$–$C_4$-alkenylene, or a pharmaceutically acceptable salt thereof.

Preferred compounds are those of formula (I), wherein

R¹ denotes hydrogen or $C_1$–$C_6$-alkyl, being optionally substituted by $C_3$–$C_6$-cycloylalkyl;

R² and R³ together with the nitrogen form a 6-membered saturated or unsaturated heterocyclic ring which may contain nitrogen as an additional heteroatom, whilst the heterocyclic ring is substituted by a group selected from phenyl, pyridinyl, pyrimidinyl, benzimidizalonyl, and substituted phenyl being mono- or di-substituted by a group selected from $CF_3$, $CH_3$, $OCH_3$, F, and Cl;

A $C_2$–$C_4$-alkenylene, or a pharmaceutically acceptable salt thereof.

Also of interest are compounds of formula (I), wherein

R¹ denotes hydrogen or $C_1$–$C_4$-alkyl, being optionally substituted by cyclohexyl;

R² and R³ together with the nitrogen form a 6-membered saturated or unsaturated heterocyclic ring which may contain nitrogen as an additional heteroatom, whilst the heterocyclic ring is substituted by a group selected from pyridyl, pyrimidinyl, phenyl, and substituted phenyl being mono- or di-substituted by a group selected from $CF_3$, $CH_3$, $OCH_3$, F, and Cl;

A butenylene, or a pharmaceutically acceptable salt thereof.

Of particular interest are compounds of formula (I), wherein

R¹ denotes hydrogen, methyl, ethyl, n-propyl, or cyclohexylmethyl;

R² and R³ together with the nitrogen form a ring selected from the group consisting of piperazine, piperidine, and tetrahydropyridine, which is substituted by a group selected from pyridyl, pyrimidinyl, phenyl, and substituted phenyl being mono- or di-substituted by a group selected from $CF_3$, $CH_3$, and Cl;

A butenylene, or a pharmaceutically acceptable salt thereof.

Furthermore preferred are compounds of formula (I), wherein

R¹ denotes hydrogen, methyl, n-propyl, or cyclohexylmethyl;

R² and R³ together with the nitrogen form a piperazine ring, being substituted by a group selected from trifluoromethylphenyl, chlorophenyl, pyridyl, and pyrimidinyl;

A butenylene, or a pharmaceutically acceptable salt thereof.

The most preferred compounds according to the invention are:

(a) 1-Methyl-3-(4-{4-[3-(trifluoromethyl)phenyl]piperazin-1-yl}-(2Z)-butenyl)-1,3-dihydro-2H-benzimidazol-2-one;

(b) 1-n-Propyl-3-(4-{4-[3-(trifluoromethyl)phenyl]piperazin-1-yl}-(2Z)-butenyl)-1,3-dihydro-2H-benzimidazol-2-one;

(c) 1-Methyl-3-(4-{4-[3-(trifluoromethyl)phenyl]piperazin-1-yl}-(2E)-butenyl)-1,3-dihydro-2H-benzimidazol-2-one; and (d) 1-Cyclohexylmethyl-3-(4-{4-[2-pyridyl]piperazin-1-yl}-(2E)-butenyl)-1,3-dihydro-2H-benzimidazol-2-one.

If required, the compounds of general formulae (I) may be converted into the salts thereof, particularly, for pharmaceutical use, into the pharmaceutically acceptable salts thereof with an inorganic or organic acid. Suitable acids for this purpose include hydrochloric acid, hydrobromic acid, sulfuric acid, phosphoric acid, methanesulfonic acid, acetic acid, fumaric acid, succinic acid, lactic acid, citric acid, tartaric acid, or maleic acid. Moreover, mixtures of these acids may be used.

The alkyl groups meant here (including those which are components of other groups) are branched and unbranched alkyl groups having 1 to 6 carbon atoms, preferably 1 to 4 carbon atoms, such as methyl, ethyl, n-propyl, isopropyl, butyl, isobutyl, sec-butyl, tert-butyl, pentyl, isopentyl, and hexyl.

The alkylene groups meant here are branched and unbranched alkyl-bridges having 1 to 6 carbon atoms, preferably 1 to 4 carbon atoms, such as methylene, ethylene, n-propylene, isopropylene, butylene, isobutylene, sec-butylene, tert-butylene, pentylene, isopentylene, and hexylene.

Alkenyl groups (including those which are components of other groups) are the branched and unbranched alkenyl groups with 2 to 6 carbon atoms, preferably 2 to 4 carbon atoms, provided that they have at least one double bond, e.g., the alkyl groups mentioned above provided that they have at least one double bond, such as, for example, vinyl (provided that no unstable enamines or enolethers are formed), propenyl, isopropenyl, butenyl, pentenyl, and hexenyl.

Alkenylene groups are the branched and unbranched alkenyl-bridges with 2 to 6 carbon atoms, preferably 2 to 4 carbon atoms, provided that they have at least one double bond, e.g., the alkylene groups mentioned above provided that they have at least one double bond, such as, for example, vinylene (provided that no unstable enamines or enolethers are formed), propylene, isopropenylene, butenylene, pentenylene, and hexenylene.

If not otherwise specified the alkenyl and alkenylene groups mentioned above are to be understood as embracing optionally existing stereoisomers. Accordingly, for instance, the definition 2-butenyl is to be understood as embracing 2-(Z)-butenyl and 2-(E)-butenyl, etc.

The term alkynyl groups (including those which are components of other groups) refers to alkynyl groups having 2 to 6, preferably 2 to 4 carbon atoms provided that they have at least one triple bond, e.g., ethynyl, propargyl, butynyl, pentynyl, and hexynyl.

$C_3$–$C_6$-cycloalkyl residues are, for example, cyclopropyl, cyclobutyl, cyclopentyl, or cyclohexyl, which can also be substituted with branched or non-branched alkyl with 1–4 carbon atoms, hydroxy, and/or halogen or as defined above.

Examples of N-linked 5- or 6-membered heterocyclic rings of general formula $NR^2R^3$ are as follows: pyrrole, pyrroline, pyrrolidine, piperidine, piperazine, morpholine, imidazole, imidazoline, imidazolidine, pyrazole, pyrazoline, pyrazolidine, preferably morpholine, piperazine, and piperidine.

Examples of saturated or unsaturated bi- or tricyclic heterocyclic ring system of formula $NR^2R^3$ which may contain nitrogen or oxygen as an additional heteroatom, are as follows: indole, tetrahydroindole, benzimidazole, benzoxazole, 1,2-dihydrochinoline, 1,2-dihydroisochinoline, β-carboline, 9H-1,2,3,4-tetrahydropyridoindole, and 9,10-dihydroacridine.

Halogen stands for fluorine, chlorine, bromine, or iodine, preferably chlorine or bromine.

"=O" means an oxygen atom linked by a double bond.

The compounds of general formula (I) may be conveniently prepared by a variety of synthetic processes analogous to those known in the art using conventional methods. For example these compounds may be prepared by alkylating the suitable secondary amine (III) with the proper benzimidazolone (II) bearing in the alkyl or alkenyl side chain suitable leaving group X such as halogen, methanesulfonate or 4-methylbenzenesulfonate (scheme 1).

Scheme 1

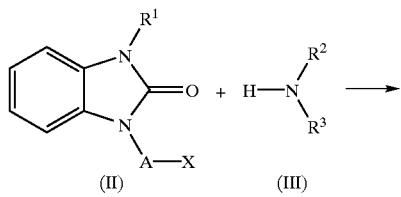

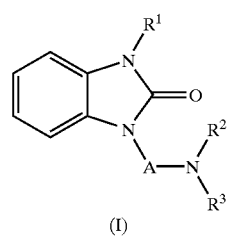

Scheme 1

The reaction conditions for the conventional synthesis of compounds of formula (I) according to scheme 1 are disclosed in EP 526 434 A1. Said reference additionally describes the possible synthetic pathways for the preparation of starting compounds (II).

According to a second option, the reaction sequence according to scheme 1 can not only be conducted via the conventional synthetic methods outlined in EP 526 434 A1 but, in the alternative, via combinatorial chemistry. For this approach a set of N-alkyl-N'-halo alkyl/alkenyl benzimidazolones of formula (II) (from now on identified as Building Blocks or BB; see Table 1) was prepared via the traditional methods described in EP 526 434 A1 and then combinatorially reacted with the suitable secondary amines of formula (III) (Table 2).

The process was carried out in a special apparatus consisting of a lower vial (reacting chamber) and an upper vial (condenser). Each compound was reacted with each amine in DMF under stirring at a temperature between 40° C. and 100° C., preferably at 60° C., for 6 to 8 hours in the presence of $Na_2CO_3$. The excess amine was then scavenged at room temperature by introducing a polystyrene isocyanatemethyl resin of formula (IV) able to catch the excess amine as an urea of formula (V) immobilized on the solid support (Scheme 2).

Scheme 2

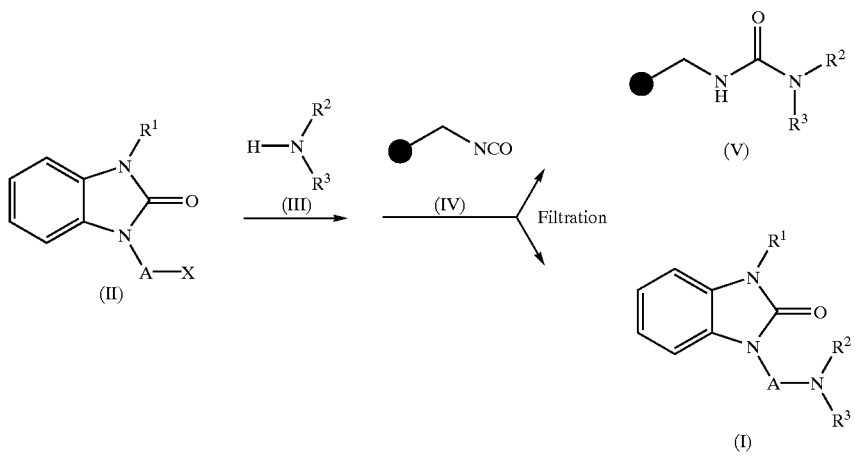

Scheme 2

The upper part of the reaction apparatus is substituted with another vial containing a frit inside and a connection to the vacuum. Filtration after turning over the apparatus and evaporation to dryness afforded the desired compounds of formula (I) in excellent yield and good purity. The parallel application of the aforementioned process to all of the compounds of formula (II) as shown in Table 1 and all of the selected amines (III) as shown in Table 2 allows the efficient synthesis of all of the compounds (I) according to the present invention.

TABLE 1

Building Blocks (BB) of Formula (II) Subjected to the Process of Scheme 2

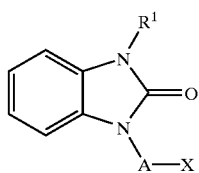

(II)

| Building Block No. | Structure | Building Block No. | Structure |
|---|---|---|---|
| BB01 | 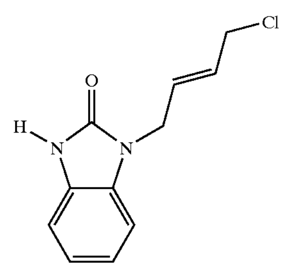 | BB02 | 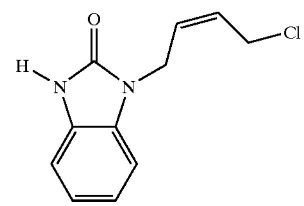 |
| BB03 | 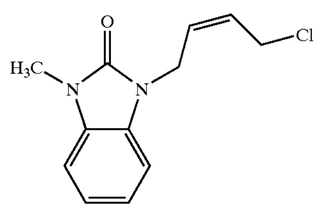 | BB04 | 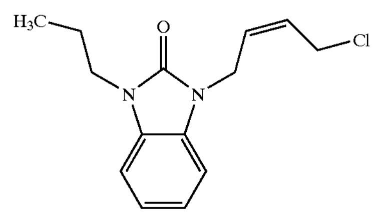 |
| BB05 | 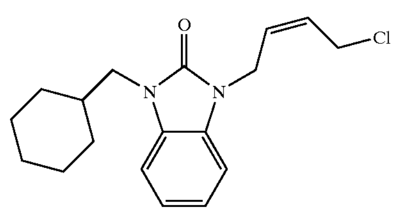 | BB06 | 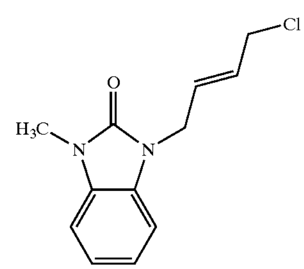 |
| BB07 | 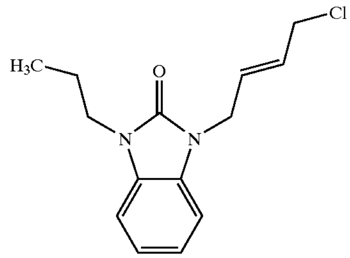 | BB08 | 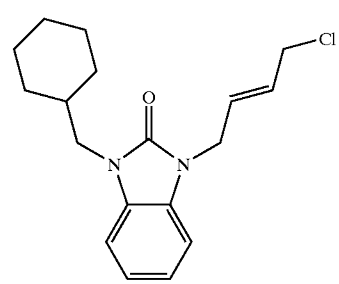 |

TABLE 2

Amines (AM) of Formula (III) Subjected to the Process of Scheme 2

$$H-N\begin{smallmatrix}R^2\\R^3\end{smallmatrix}$$ (III)

| Amine No. | Structure | Amine No. | Structure |
|---|---|---|---|
| AM01 | HN-piperazine-N-phenyl | AM02 | HN-piperazine-N-CH(phenyl)(4-Cl-phenyl) |
| AM03 | HN-piperazine-N-CH2-phenyl | AM04 | HN-piperazine-N-(2-pyridyl) |
| AM05 | HN-piperazine-N-(3-Cl-phenyl) | AM06 | HN-piperazine-N-(2-pyrimidyl) |
| AM07 | 2,3,4,5-tetrahydro-1H-pyrido[3,4-b]indole | AM08 | HN-piperazine-N-(3,5-dichloropyridin-4-yl) |
| AM09 | HN-piperazine-N-(3-CF3-phenyl) | AM10 | HN-tetrahydropyridine-4-phenyl |
| AM11 | HN-piperazine-N-(3,4-dichlorophenyl) | AM12 | HN-piperidine-N-(2-oxo-2,3-dihydrobenzimidazol-1-yl) |
| AM13 | HN-piperidine-4-OH-4-(3-CF3-4-Cl-phenyl) | AM14 | HN-piperazine-N-(4-OMe-phenyl) |

TABLE 2-continued

Amines (AM) of Formula (III) Subjected to the Process of Scheme 2

(III)

| Amine No. | Structure | Amine No. | Structure |
|---|---|---|---|
| AM15 | 4-chlorobenzyl piperazine | AM16 | 1-phenyl-1,3,8-triazaspiro[4.5]decan-4-one |
| AM17 | benzo[1,3]dioxol-5-ylmethyl piperazine | AM18 | 1-(2,3-dimethylphenyl)piperazine |
| AM19 | 1-(2-methoxyphenyl)piperazine | AM20 | 1-(3-methylphenyl)piperazine |
| AM21 | 1-(2-methylphenyl)piperazine | AM22 | 1-(2-chlorophenyl)piperazine |

For pharmaceutical use, the compounds of general formula (I) may be used as such or in the form of physiologically acceptable acid addition salts. The term "physiologically acceptable acid addition salts" includes the salts resulting from both organic and inorganic acids such as maleic, citric tartaric, methanesulfonic, acetic, benzoic, succinic, gluconic, isethionic, glycinic, lactic, malic, mucoic, glutammic, sulfamic, and ascorbic acids; inorganic acids include hydrochloric, hydrobromic, nitric, sulfuric, or phosphoric acid.

According to a further feature of the present invention there are provided pharmaceutical compositions comprising as an active ingredient at least one compound of formula (I), as before defined, or a physiologically acceptable addition salt thereof in addition with one or more pharmaceutical carriers, diluents or excipients. For pharmaceutical administration the compounds of general formula (I) and their physiologically acceptable acid addition salts may be incorporated into the conventional pharmaceutical preparation in solid, liquid, or spray form. The composition may, for example, be presented in a form suitable for oral, rectal, parenteral administration, or for nasal inhalation: preferred forms includes for example, capsules, tablets, coated tables, ampoules, suppositories, and nasal spray.

The active ingredient may be incorporated in excipients or carriers conventionally used in pharmaceutical compositions such as, for example, talc, arabic gum, lactose, gelatine, magnesium stearate, corn starch, aqueous or nonaqueous vehicles, polyvinyl pyrrolidone, semisynthetic glycerides of fatty acids, benzalcon chloride, sodium phosphate, EDTA, and polysorbate 80.

In case it is desired to further increase the solubility of the compounds of general formula (I) or of their physiologically acceptable salts, surfactants or nonionic surfactants such as PEG 400, cyclodextrin, metastable polymorphs, inert adsorbents such as bentonite, may be incorporated. Furthermore some techniques may be employed by preparing, for example, eutectic mixtures and/or solid dispersion by using mannitol, sorbitol, saccharose, or succinic acid, or physically-modified forms by using hydrosoluble polymers, PVP, or PEG 4000–20,000. The compositions are advantageously formulated in dosage units, each dosage unit being adapted to supply a single dose of the active ingredient. Each dosage unit may conveniently contain from 0.01 mg to 100 mg, preferably from 0.1 mg to 50 mg.

However, it could be necessary to depart from the cited amounts, depending on the body weight or on the administration route, on the individual response to the medicament, on the type of formulation and on the time, or time range, in which the administration is carried out. Therefore, it can be sufficient, in some cases, to use a lower amount then the cited minimum amount, whereas in other cases the higher range could be exceeded. When administering higher amounts, it would be advisable to subdivide them in repeated administrations during the day. Moreover, the compounds of general formula (I) or the acid addition salts thereof can also be combined with other, different active substances.

The following examples illustrate the present invention, without limiting the scope thereof.

Examples of Pharmaceutical Formulations

A. Tablets Containing 100 mg of Active Substance

| Component | Amount per tablet (mg) |
| --- | --- |
| active substance | 100 |
| lactose | 140 |
| maize starch | 240 |
| polyvinylpyrrolidone | 15 |
| magnesium stearate | 5 |
| TOTAL | 500 |

The finely ground active substance, lactose are part of maize starch are mixed. The mixture is sieved, wetted with a solution of polyvinylpyrrolidone in water, kneaded, finely granulated, and dried. The granulate, the remaining maize starch and magnesium stearate are sieved and mixed together. The mixture is compressed to tablets of suitable form and size.

B. Tablets Containing 80 mg of Active Substance

| Component | Amount per tablet (mg) |
| --- | --- |
| active substance | 80 |
| lactose | 55 |
| maize starch | 190 |
| polyvinylpyrrolidone | 15 |
| sodium carboxymethyl starch | 23 |
| magnesium stearate | 2 |
| TOTAL | 400 |

The finely ground active substance, part of the maize starch, lactose, microcrystalline cellulose, and polyvinylpyrrolidone are mixed. The mixture is sieved and worked up with the remaining maize starch and water to obtain a granulate, which is dried and sieved. This is added with sodium carboxymethyl starch and magnesium stearate and mixed, then the mixture is compressed to tablets of suitable size.

C. Solutions for Vials

| Component | Amount |
| --- | --- |
| active substance | 50 mg |
| sodium chloride | 50 mg |
| water for injection | 5 ml |

The active substance is dissolved in water, optionally at pH of 5.5 to 6.5, and treated with sodium chloride as an osmolality agent. The resulting solution is filtered apyrogenically, and the filtrate is placed in vials under aseptic conditions, then vials are sterilized and flame sealed. The vials may contain, e.g., 5 mg, 25 mg, and 50 mg of active substance.

Experimental

The following examples illustrate the preparation of all the new compounds included in the present invention. It should be understood that the invention is not limited to the given examples of chemical methods and processes for the preparation of the substances, as other conventional methods well known to those skilled in the art, are suitable too. In the following descriptions, each of the 8 Building Blocks prepared is identified by its relevant Tag.

A. Preparation of the Building Blocks (BB) of Formula (II)

Description 1

[BB01]: 1-[(2E)-4-chloro-2-butenyl]-1,3-dihydro-2H-benzimidazol-2-one

Phenyl-2-oxo-2,3-dihydro-1H-benzimidazole-2-carboxylate (10 g, 39 mmoles) was added to a suspension of 50% sodium hydride (2.3 g, 47 mmoles) in DMF (100 ml). The reaction mixture was stirred for 30 minutes at room temperature, then trans-1,4-dichloro-2-butene (5.5 ml; 52 mmoles) was added dropwise and the reaction mixture was heated at 90° C. for 3 hours. After cooling, an aqueous 10% KOH solution was added and the reaction mixture was stirred for 1 hour. The reaction mixture was then poured into water, extracted with ethyl acetate, and the organic layer washed with a 5% aqueous HCl solution. The organic layer was taken to dryness and the crude compound was purified by flash chromatography (cyclohexane-ethyl acetate 50-50) to give 2.3 g of the title compound as a white solid; m.p. 120° C.

According to the above described procedure, the following compound was prepared from the suitable intermediates:

[BB02]: 1-[(2Z)-4-chloro-2-butenyl]-1,3-dihydro-2H-benzimidazol-2-one

The crude compound was purified by flash chromatography (cyclohexane-ethyl acetate 50-50) to give 0.8 g of the title compound as a white solid. m.p. 105° C.

Description 2

1-methyl-1,3-dihydro-2H-benzimidazol-2-one

A solution of 1-isopropenyl-1,3-dihydro-2H-benzimidazol-2-one (30 g, 0.172 moles) in DMF (180 ml) was added dropwise over 30 minutes to a suspension of 80% sodium hydride (5.42 g, 0.181 moles) in DMF (60 ml). The reaction mixture was heated at 45° C. for 45 minutes then a solution of methyl iodide (16.1 ml, 0.258 moles) in DMF (50 ml) was added dropwise. The reaction mixture was heated at 80° C. to 90° C. for 45 minutes, cooled at room temperature and adjusted to pH 3 to 4 with 37% HCl and heated at 80° C. for 30 minutes. The reaction mixture was cooled at room temperature and poured into ice/water. The solid residue separated was filtered and dried to give 19 g of the title compound, m.p. 188° C.–190° C.

According to the above described procedure, the following compounds were prepared:

1-propyl-1,3-dihydro-2H-benzimidazol-2-one 27 g, m.p. 92° C.–94° C.

1-(cyclohexylmethyl)-1,3-dihydro-2H-benzimidazol-2-one 32.5 g, m.p. 175° C.–180° C.

Description 3

[BB03]: 1-[(2Z)-4-chloro-2-butenyl]-3-methyl-1,3-dihydro-2H-benzimidazol-2-one

A solution of 1-methyl-1,3-dihydro-2H-benzimidazol-2-one (2 g, 13 mmoles) in DMF (50 ml) was added dropwise and at room temperature to a suspension of 80% sodium hydride (0.4 g, 13 mmoles) in DMF (25 ml). The mixture was heated at 40° C. for 30 minutes and cis-1,4-dichloro-2-butene (2.84 ml, 27 mmoles) in DMF (30 ml) was dropped in 4 hours under stirring. After stirring overnight at room temperature, the reaction mixture was poured into ice water and extracted with ethyl acetate. The organic layer was evaporated and the crude residue was purified by flash chromatography (hexane-ethyl acetate 55-45) to give 1.4 of the title compound as a thick yellowish oil.

According to the above described procedure, the following compounds were prepared:

[BB04]: 1-[(2Z)-4-chloro-2-butenyl]-3-propyl-1,3-dihydro-2H-benzimidazol-2-one

The crude compound was purified by flash chromatography (hexane-ethyl acetate 70-30). 1.35 g, clear oil.

[BB05]: 1-[(2Z)-4-chloro-2-butenyl]-3-(cyclohexylmethyl)-1,3-dihydro-2H-benzimidazol-2-one The crude compound was purified by flash chromatography (hexane-ethyl acetate 70-30). 2.4 g, white solid; m.p. 73° C.–76° C.

[BB06]: 1-[(2E)-4-chloro-2-butenyl]-3-methyl-1,3-dihydro-2H-benzimidazol-2-one

The crude compound was purified by flash chromatography (hexane-ethyl acetate 55-45). 2.8 g, light brown oil.

[BB07]: 1-[(2E)-4-chloro-2-butenyl]-3-propyl-1,3-dihydro-2H-benzimidazol-2-one

The crude compound was purified by flash chromatography (hexane-ethyl acetate 65-35). 2 g, thick yellowish oil.

[BB08]: 1-[(2E)-4-chloro-2-butenyl]-3-(cyclohexylmethyl)-1,3-dihydro-2H-benzimidazol-2-one The crude compound was purified by flash chromatography (hexane-ethyl acetate 70-30). 2.75 g, colorless thick oil.

B. General Method for the Preparation of the Compounds of Formula (I)

A solution of each building block (II) (0.1 mM) was reacted under stirring with each amine (0.2 mM) in anhydrous DMF (100 μl) in the presence of $Na_2CO_3$ (0.3 mM) at a temperature ranging from room temperature to 100° C., preferably between 60° C and 80° C., for about 6 to 8 hours. Isocyanatemethyl Polystyrene Resin (loading 0.23 meq/g), (0.2 mM) was introduced and the mixture was gently stirred at room temperature for 8 hours. The resin was then filtered off under vacuum, washed with DMF, and filtered again. The collected solutions were evaporated to dryness in a speed-vac centrifuge.

Table 3 collects the structural formula of the synthesized compounds along with the corresponding characterizing mass data (i.e., $[M+H]^+$) obtained for each of the compounds according to the invention. The identification of the compounds and their purity was carried out by using positive APCI-LC/MS technique.

TABLE 3

Compounds of General Formula (I)

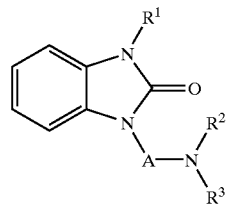

(I)

| Compound No. | —$R^1$ | —A— |  | $[M + H]^+$ |
|---|---|---|---|---|
| 1 | —H |  |  | 349 |

TABLE 3-continued
Compounds of General Formula (I)
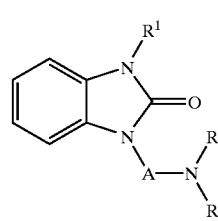
(I)
| Compound No. | —R¹ | —A— | —N(R²)(R³) | [M + H]⁺ |
|---|---|---|---|---|
| 2 | —H |  | 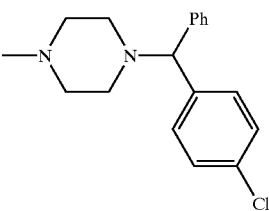 (piperazine with -CH(Ph)(4-ClC₆H₄)) | 473 |
| 3 | —H | 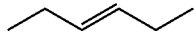 | 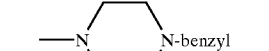 (N-benzylpiperazine) | 363 |
| 4 | —H | 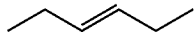 |  (1-(2-pyridyl)piperazine) | 350 |
| 5 | —H |  |  (1-(3-chlorophenyl)piperazine) | 383 |
| 6 | —H | 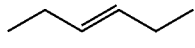 | 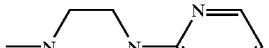 (1-(2-pyrimidinyl)piperazine) | 351 |
| 7 | —H | 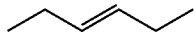 | 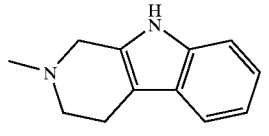 (tetrahydro-β-carboline) | 359 |
| 8 | —H | 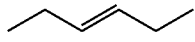 | 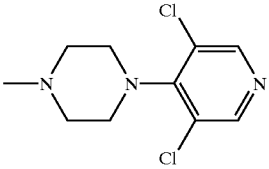 (1-(3,5-dichloro-4-pyridyl)piperazine) | 418 |
| 9 | —H |  | 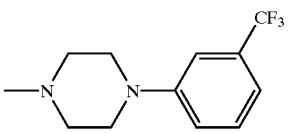 (1-(3-trifluoromethylphenyl)piperazine) | 417 |

TABLE 3-continued
Compounds of General Formula (I)
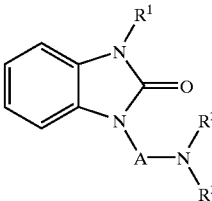
| Compound No. | —R¹ | —A— | —N(R²)(R³) | [M + H]⁺ |
|---|---|---|---|---|
| 10 | —H |  | 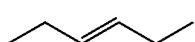 | 346 |
| 11 | —H | 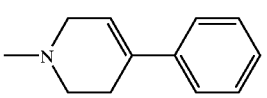 | 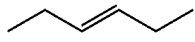 | 417 |
| 12 | —H | 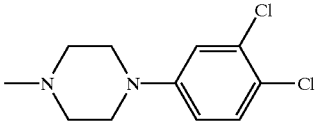 | 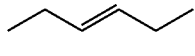 | 404 |
| 13 | —H | 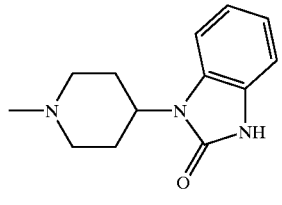 | 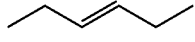 | 466 |
| 14 | —H | 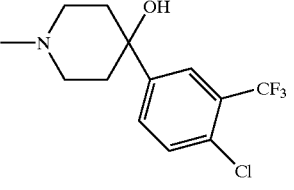 | 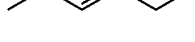 | 379 |
| 15 | —H | 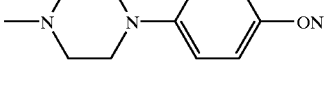 |  | 397 |
| 16 | —H | 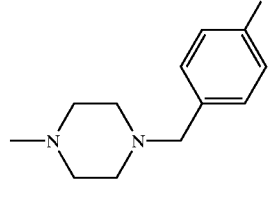 |  | 418 |

TABLE 3-continued
Compounds of General Formula (I)
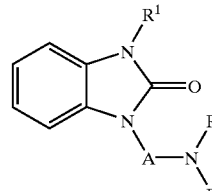
(I)
| Compound No. | —R¹ | —A— | —N(R²)(R³) | [M + H]⁺ |
|---|---|---|---|---|
| 17 | —H |  | 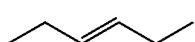 | 407 |
| 18 | —H | 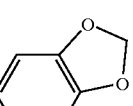 | 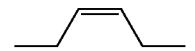 | 349 |
| 19 | —H | 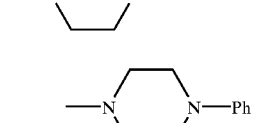 |  | 473 |
| 20 | —H | 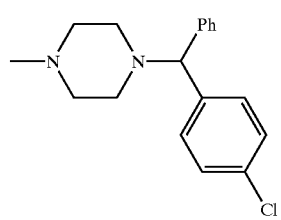 | 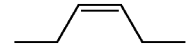 | 363 |
| 21 | —H |  |  | 350 |
| 22 | —H | 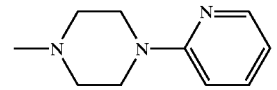 |  | 383 |
| 23 | —H | 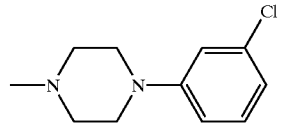 |  | 351 |
| 24 | —H | 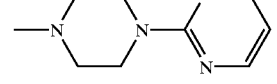 | 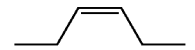 | 359 |

TABLE 3-continued

Compounds of General Formula (I)

(I)

| Compound No. | —R¹ | —A— | —N(R²)(R³) | [M + H]⁺ |
|---|---|---|---|---|
| 25 | —H | cis-CH₂-CH=CH-CH₂— | N-methylpiperazinyl-(3,5-dichloropyridin-4-yl) | 418 |
| 26 | —H | cis-CH₂-CH=CH-CH₂— | N-methylpiperazinyl-(3-trifluoromethylphenyl) | 417 |
| 27 | —H | cis-CH₂-CH=CH-CH₂— | 4-phenyl-1,2,3,6-tetrahydropyridin-1-yl | 346 |
| 28 | —H | cis-CH₂-CH=CH-CH₂— | N-methylpiperazinyl-(3,4-dichlorophenyl) | 417 |
| 29 | —H | cis-CH₂-CH=CH-CH₂— | 1-(2-oxo-2,3-dihydro-1H-benzimidazol-1-yl)piperidin-4-yl | 404 |
| 30 | —H | cis-CH₂-CH=CH-CH₂— | 4-hydroxy-4-(4-chloro-3-trifluoromethylphenyl)piperidin-1-yl | 466 |
| 31 | —H | cis-CH₂-CH=CH-CH₂— | N-methylpiperazinyl-(4-nitrosophenyl) | 379 |

TABLE 3-continued
Compounds of General Formula (I)
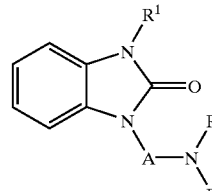
(I)
| Compound No. | —R¹ | —A— | —N(R²)(R³) | [M + H]⁺ |
|---|---|---|---|---|
| 32 | —H | 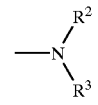 | 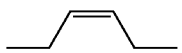 | 397 |
| 33 | —H | 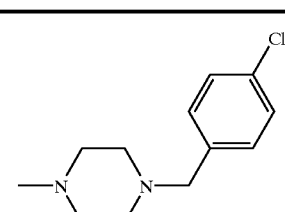 | 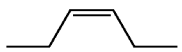 | 418 |
| 34 | —H | 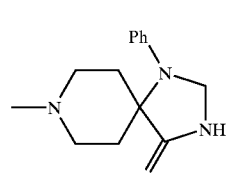 | 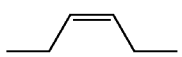 | 407 |
| 35 | -Methyl | 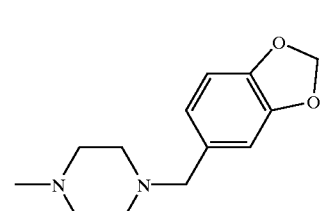 | 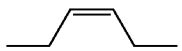 | 363 |
| 36 | -Methyl | 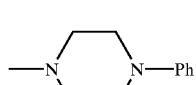 | 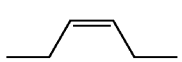 | 487 |
| 37 | -Methyl | 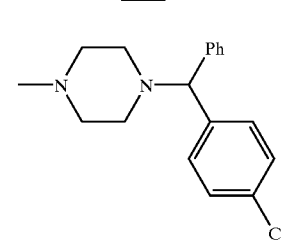 |  | 377 |
| 38 | -Methyl | 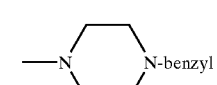 |  | 364 |

TABLE 3-continued
Compounds of General Formula (I)
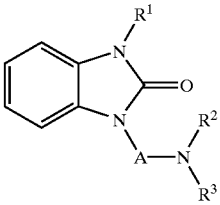
(I)
| Compound No. | —R¹ | —A— | —N(R²)(R³) | [M + H]⁺ |
|---|---|---|---|---|
| 39 | -Methyl | 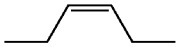 | 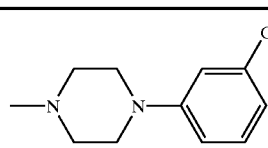 | 397 |
| 40 | -Methyl |  | 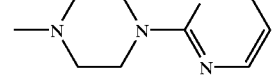 | 365 |
| 41 | -Methyl |  | 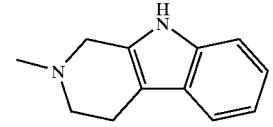 | 373 |
| 42 | -Methyl |  | 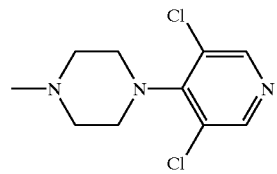 | 432 |
| 43 | -Methyl |  | 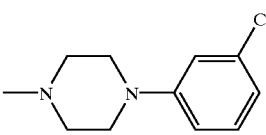 | 431 |
| 44 | -Methyl |  | 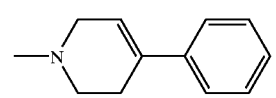 | 360 |
| 45 | -Methyl |  | 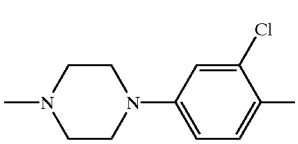 | 431 |
| 46 | -Methyl |  | 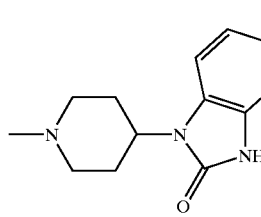 | 418 |

TABLE 3-continued
Compounds of General Formula (I)
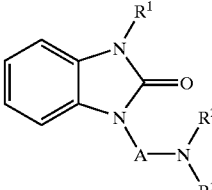
| Compound No. | —R¹ | —A— | —N(R²)(R³) | [M + H]⁺ |
|---|---|---|---|---|
| 47 | -Methyl |  |  | 480 |
| 48 | -Methyl | 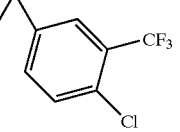 | 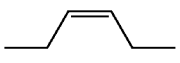 | 393 |
| 49 | -Methyl | 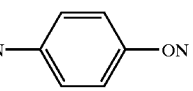 |  | 411 |
| 50 | -Methyl | 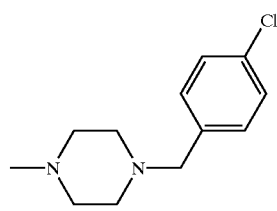 |  | 432 |
| 51 | -Methyl | 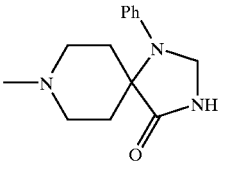 |  | 421 |
| 52 | -n-Propyl | 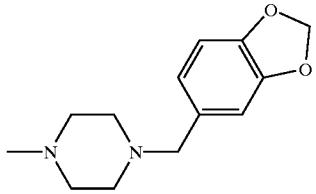 |  | 391 |
| 53 | -n-Propyl | 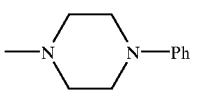 | 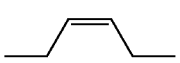 | 515 |

TABLE 3-continued

Compounds of General Formula (I)

| Compound No. | —R¹ | —A— | −N(R²)(R³) | [M + H]⁺ |
|---|---|---|---|---|
| 54 | -n-Propyl | -CH₂-CH=CH-CH₂- (cis) | piperazine-N-benzyl | 405 |
| 55 | -n-Propyl | -CH₂-CH=CH-CH₂- (cis) | piperazine-N-(2-pyridyl) | 392 |
| 56 | -n-Propyl | -CH₂-CH=CH-CH₂- (cis) | piperazine-N-(3-chlorophenyl) | 425 |
| 57 | -n-Propyl | -CH₂-CH=CH-CH₂- (cis) | piperazine-N-(2-pyrimidyl) | 393 |
| 58 | -n-Propyl | -CH₂-CH=CH-CH₂- (cis) | 2-methyl-1,2,3,4-tetrahydro-β-carboline | 401 |
| 59 | -n-Propyl | -CH₂-CH=CH-CH₂- (cis) | piperazine-N-(3,5-dichloro-4-pyridyl) | 460 |
| 60 | -n-Propyl | -CH₂-CH=CH-CH₂- (cis) | piperazine-N-(3-trifluoromethylphenyl) | 459 |
| 61 | -n-Propyl | -CH₂-CH=CH-CH₂- (cis) | 4-phenyl-1,2,3,6-tetrahydropyridine | 388 |
| 62 | -n-Propyl | -CH₂-CH=CH-CH₂- (cis) | piperazine-N-(3,4-dichlorophenyl) | 459 |

US 6,586,435 B2
TABLE 3-continued
Compounds of General Formula (I)
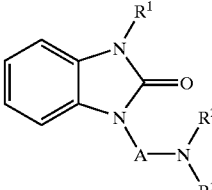
| Compound No. | —R¹ | —A— | —N(R²)(R³) | [M + H]⁺ |
|---|---|---|---|---|
| 63 | -n-Propyl |  | 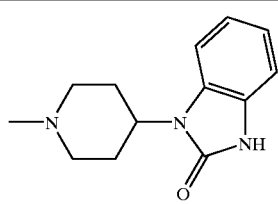 | 446 |
| 64 | -n-Propyl |  | 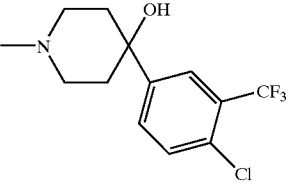 | 508 |
| 65 | -n-Propyl |  | 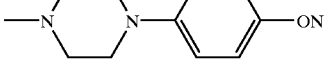 | 421 |
| 66 | -n-Propyl |  | 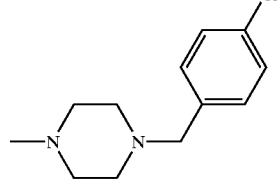 | 439 |
| 67 | -n-Propyl |  | 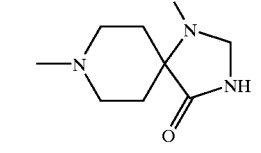 | 460 |
| 68 | -n-Propyl |  | 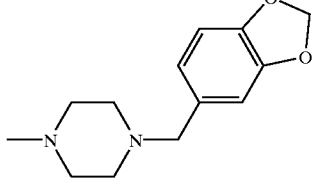 | 449 |
| 69 | 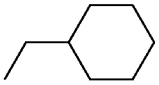 |  |  | 445 |

TABLE 3-continued

Compounds of General Formula (I)

| Compound No. | —R¹ | —A— | —N(R²)(R³) | [M + H]⁺ |
|---|---|---|---|---|
| 70 | ethylcyclohexyl | cis-CH₂-CH=CH-CH₂- | 4-[(4-chlorophenyl)(phenyl)methyl]piperazin-1-yl | 569 |
| 71 | ethylcyclohexyl | cis-CH₂-CH=CH-CH₂- | 4-benzylpiperazin-1-yl | 459 |
| 72 | ethylcyclohexyl | cis-CH₂-CH=CH-CH₂- | 4-(pyridin-2-yl)piperazin-1-yl | 446 |
| 73 | ethylcyclohexyl | cis-CH₂-CH=CH-CH₂- | 4-(3-chlorophenyl)piperazin-1-yl | 479 |
| 74 | ethylcyclohexyl | cis-CH₂-CH=CH-CH₂- | 4-(pyrimidin-2-yl)piperazin-1-yl | 447 |
| 75 | ethylcyclohexyl | cis-CH₂-CH=CH-CH₂- | 1,2,3,4-tetrahydro-β-carbolin-2-yl | 455 |
| 76 | ethylcyclohexyl | cis-CH₂-CH=CH-CH₂- | 4-(3,5-dichloropyridin-4-yl)piperazin-1-yl | 514 |
| 77 | ethylcyclohexyl | cis-CH₂-CH=CH-CH₂- | 4-[3-(trifluoromethyl)phenyl]piperazin-1-yl | 513 |

TABLE 3-continued
Compounds of General Formula (I)
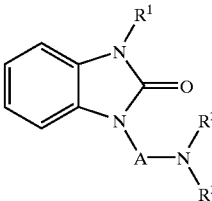
(I)
| Compound No. | —R¹ | —A— | —N(R²)(R³) | [M + H]⁺ |
|---|---|---|---|---|
| 78 |  | 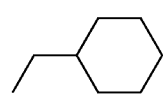 | 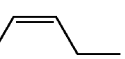 | 442 |
| 79 | 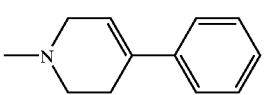 | 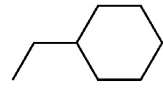 | 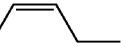 | 513 |
| 80 | 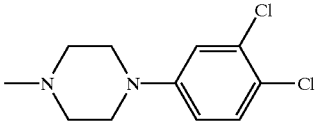 | 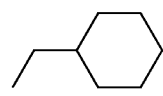 | 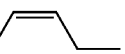 | 500 |
| 81 | 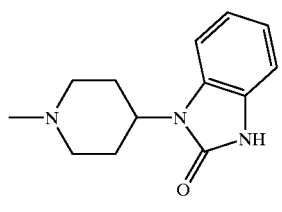 | 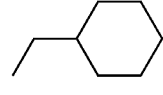 | 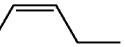 | 562 |
| 82 | 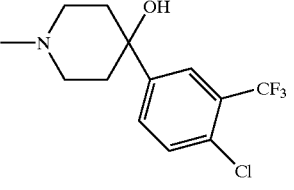 | 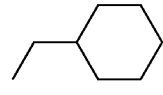 | 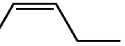 | 475 |
| 83 | 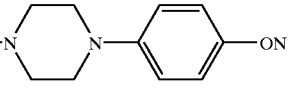 | 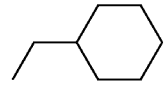 | 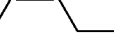 | 493 |
| 84 | 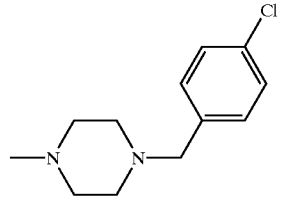 | 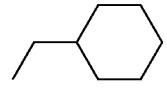 | 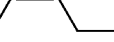 | 514 |

TABLE 3-continued

Compounds of General Formula (I)

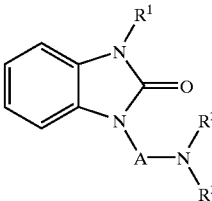

(I)

| Compound No. | —R¹ | —A— | —N(R²)(R³) | [M + H]⁺ |
|---|---|---|---|---|
| 85 | ethylcyclohexyl | CH₂-CH=CH-CH₂ | N-methylpiperazine-CH₂-benzo[1,3]dioxole | 503 |
| 86 | -Methyl | CH₂-CH=CH-CH₂ | N-methyl-N'-phenylpiperazine | 363 |
| 87 | -Methyl | CH₂-CH=CH-CH₂ | N-methylpiperazine-CH(Ph)(4-Cl-C₆H₄) | 487 |
| 88 | -Methyl | CH₂-CH=CH-CH₂ | N-methyl-N'-benzylpiperazine | 377 |
| 89 | -Methyl | CH₂-CH=CH-CH₂ | N-methyl-N'-(2-pyridyl)piperazine | 364 |
| 90 | -Methyl | CH₂-CH=CH-CH₂ | N-methyl-N'-(3-chlorophenyl)piperazine | 397 |
| 91 | -Methyl | CH₂-CH=CH-CH₂ | N-methyl-N'-(2-pyrimidinyl)piperazine | 365 |
| 92 | -Methyl | CH₂-CH=CH-CH₂ | 2-methyl-2,3,4,9-tetrahydro-1H-β-carboline | 373 |

US 6,586,435 B2
TABLE 3-continued
Compounds of General Formula (I)
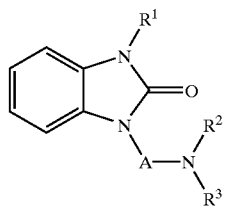
(I)
| Compound No. | —R¹ | —A— | —N(R²)(R³) | [M + H]⁺ |
|---|---|---|---|---|
| 93 | -Methyl |  | 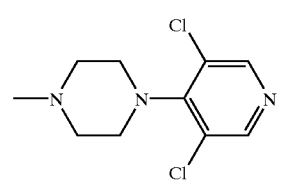 | 432 |
| 94 | -Methyl | 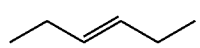 | 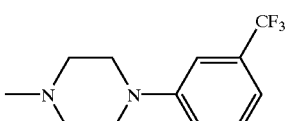 | 431 |
| 95 | -Methyl |  | 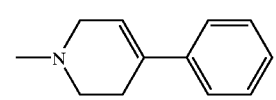 | 360 |
| 96 | -Methyl | 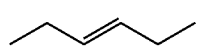 | 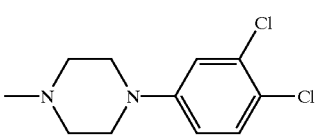 | 431 |
| 97 | -Methyl |  | 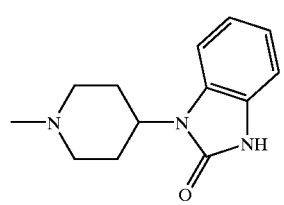 | 418 |
| 98 | -Methyl | 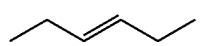 | 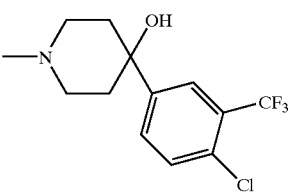 | 480 |
| 99 | -Methyl | 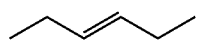 | 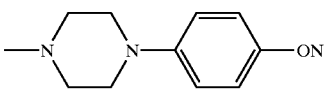 | 393 |

TABLE 3-continued
Compounds of General Formula (I)
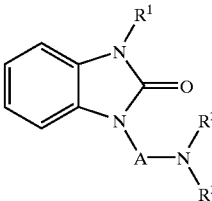
| Compound No. | —R¹ | —A— | —N(R²)R³ | [M + H]⁺ |
|---|---|---|---|---|
| 100 | -Methyl | 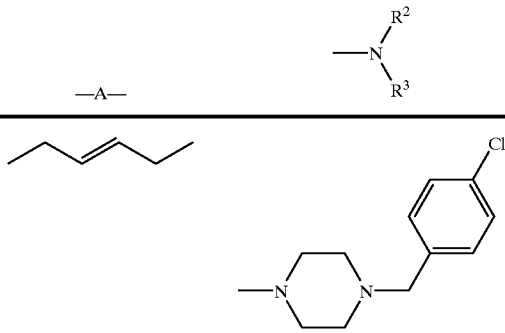 | 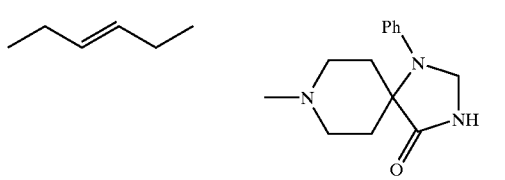 | 411 |
| 101 | -Methyl | | 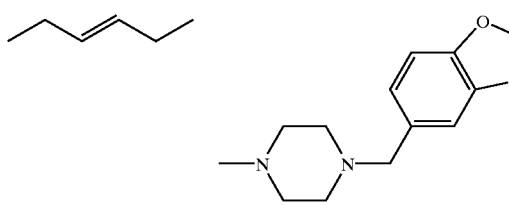 | 432 |
| 102 | -Methyl | | 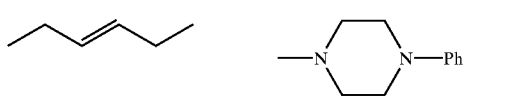 | 421 |
| 103 | -n-Propyl | | 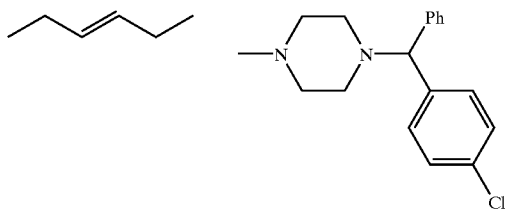 | 391 |
| 104 | -n-Propyl | | 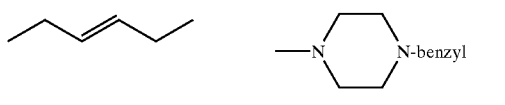 | 515 |
| 105 | -n-Propyl | | —N(piperazine)N-benzyl | 405 |
| 106 | -n-Propyl | | 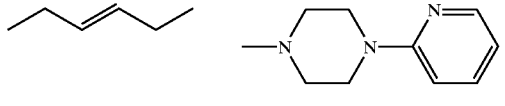 | 392 |

TABLE 3-continued

Compounds of General Formula (I)

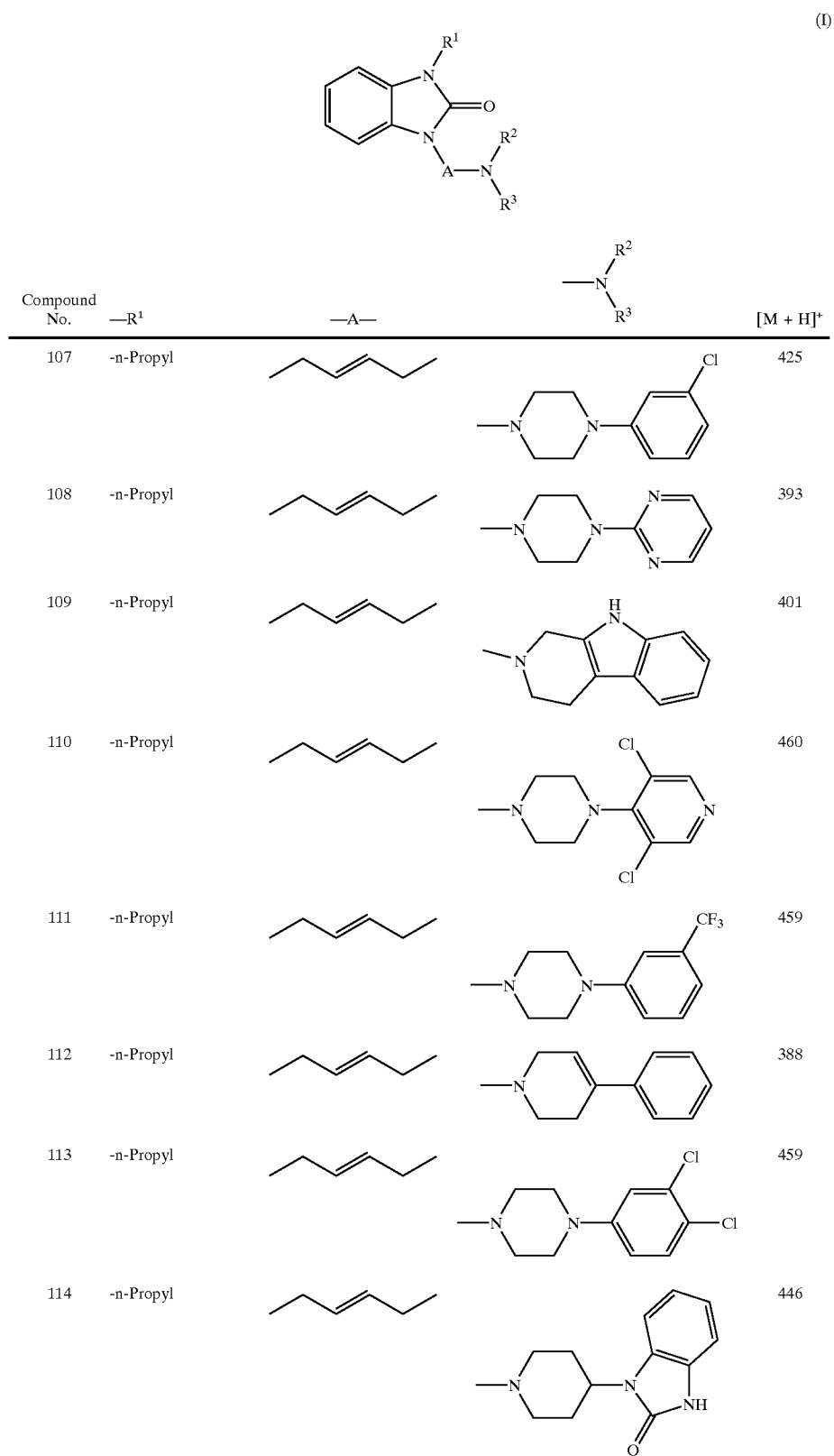

| Compound No. | —R¹ | —A— | —N(R²)(R³) | [M + H]⁺ |
|---|---|---|---|---|
| 107 | -n-Propyl | (2-butenyl) | 4-(3-chlorophenyl)-piperazin-1-yl | 425 |
| 108 | -n-Propyl | (2-butenyl) | 4-(pyrimidin-2-yl)-piperazin-1-yl | 393 |
| 109 | -n-Propyl | (2-butenyl) | 2-methyl-1,2,3,4-tetrahydro-β-carbolin-2-yl | 401 |
| 110 | -n-Propyl | (2-butenyl) | 4-(3,5-dichloropyridin-4-yl)-piperazin-1-yl | 460 |
| 111 | -n-Propyl | (2-butenyl) | 4-(3-trifluoromethylphenyl)-piperazin-1-yl | 459 |
| 112 | -n-Propyl | (2-butenyl) | 4-phenyl-1,2,3,6-tetrahydropyridin-1-yl | 388 |
| 113 | -n-Propyl | (2-butenyl) | 4-(3,4-dichlorophenyl)-piperazin-1-yl | 459 |
| 114 | -n-Propyl | (2-butenyl) | 4-(2-oxo-2,3-dihydro-1H-benzimidazol-1-yl)-piperidin-1-yl | 446 |

TABLE 3-continued
Compounds of General Formula (I)
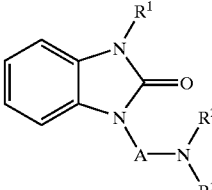
| Compound No. | —R¹ | —A— | $-N\begin{matrix}R^2\\R^3\end{matrix}$ | [M + H]⁺ |
|---|---|---|---|---|
| 115 | -n-Propyl | 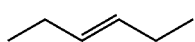 | 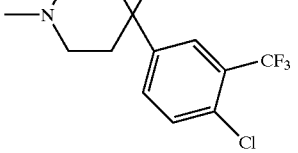 | 508 |
| 116 | -n-Propyl | 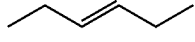 | 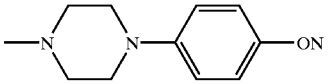 | 421 |
| 117 | -n-Propyl | 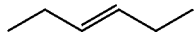 | 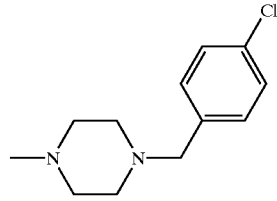 | 439 |
| 118 | -n-Propyl | 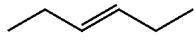 | 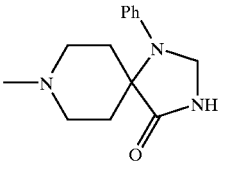 | 460 |
| 119 | -n-Propyl | 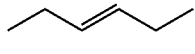 | 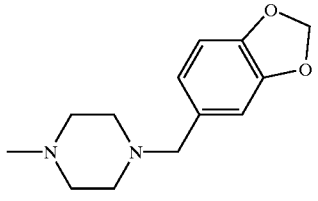 | 449 |
| 120 | 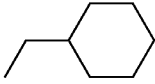 | 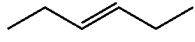 | 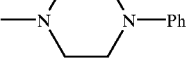 | 445 |
| 121 | 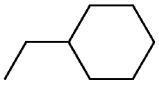 | 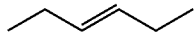 | 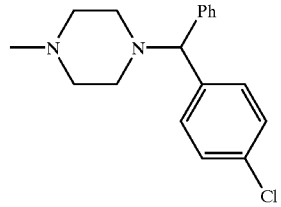 | 569 |

TABLE 3-continued

Compounds of General Formula (I)

| Compound No. | —R¹ | —A— | —N(R²)(R³) | [M + H]⁺ |
|---|---|---|---|---|
| 122 | ethylcyclohexyl | –CH₂–CH=CH–CH₂– | 4-benzylpiperazin-1-yl | 459 |
| 123 | ethylcyclohexyl | –CH₂–CH=CH–CH₂– | 4-(pyridin-2-yl)piperazin-1-yl | 446 |
| 124 | ethylcyclohexyl | –CH₂–CH=CH–CH₂– | 4-(3-chlorophenyl)piperazin-1-yl | 479 |
| 125 | ethylcyclohexyl | –CH₂–CH=CH–CH₂– | 4-(pyrimidin-2-yl)piperazin-1-yl | 447 |
| 126 | ethylcyclohexyl | –CH₂–CH=CH–CH₂– | 1,2,3,4-tetrahydro-β-carbolin-2-yl | 455 |
| 127 | ethylcyclohexyl | –CH₂–CH=CH–CH₂– | 4-(3,5-dichloropyridin-4-yl)piperazin-1-yl | 514 |
| 128 | ethylcyclohexyl | –CH₂–CH=CH–CH₂– | 4-(3-trifluoromethylphenyl)piperazin-1-yl | 513 |
| 129 | ethylcyclohexyl | –CH₂–CH=CH–CH₂– | 4-phenyl-1,2,3,6-tetrahydropyridin-1-yl | 442 |
| 130 | ethylcyclohexyl | –CH₂–CH=CH–CH₂– | 4-(3,4-dichlorophenyl)piperazin-1-yl | 513 |

TABLE 3-continued
Compounds of General Formula (I)
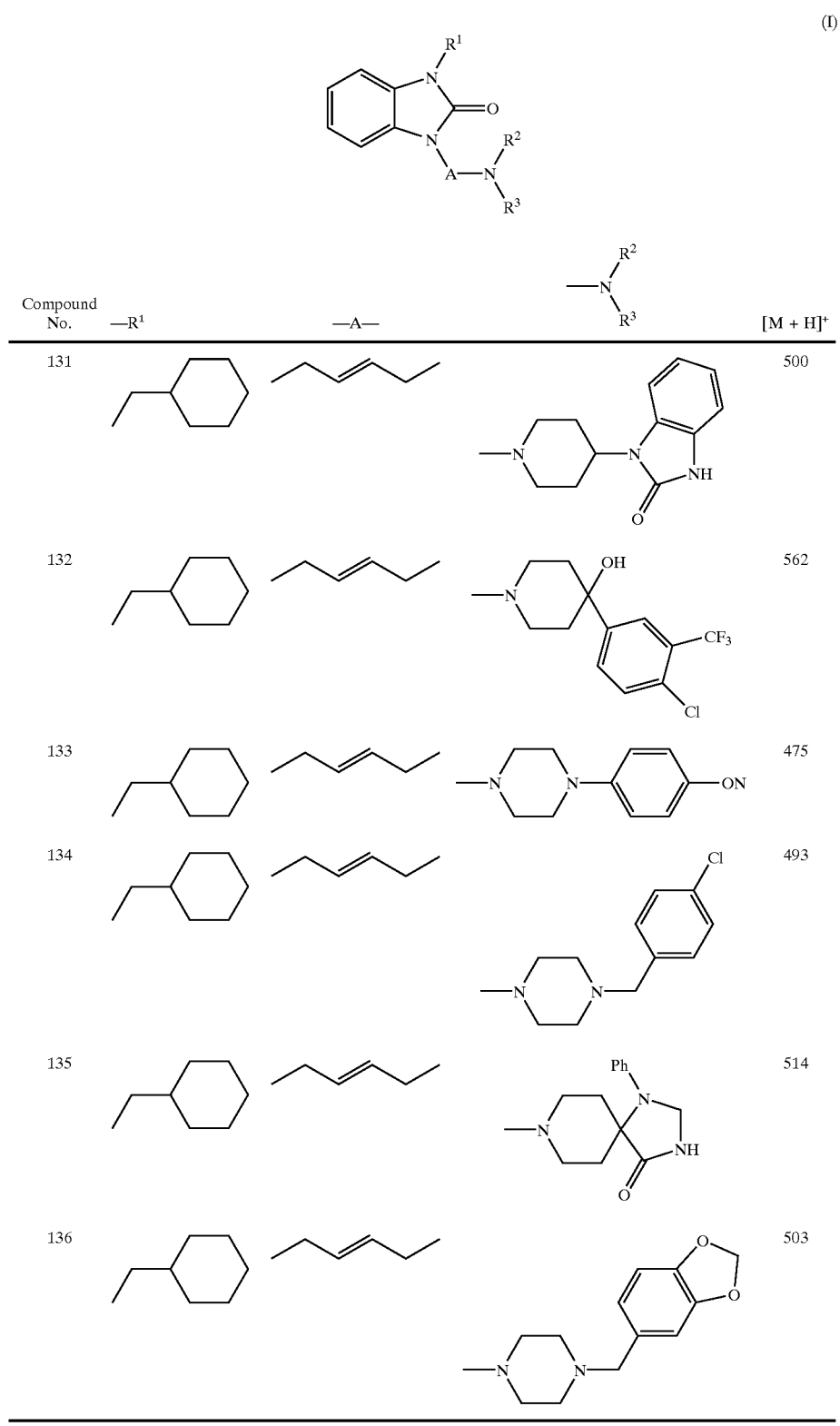
The biological profile of the compounds object of this invention, was assessed by evaluating their affinity for the 5-HT$_{1A}$, 5-HT$_{2A}$, and D$_4$ receptors, according to the methods below described.

Receptor Binding Studies

Receptor binding studies were carried out to determine the affinity of the compounds for $5\text{-HT}_{1A}$, $5\text{-HT}_{2A}$, and $D_4$ receptors

$5\text{-HT}_{1A}$, Radioligand Receptor Binding Assay

Membranes from CHO cells, expressing $5\text{-HT}_{1A}$ human receptors were suspended in incubation buffer.

Binding Assay

Binding assays were performed in MultiProbe 204 pipetting system (Packard), according to a predetermined mapping, consistent with the software Screen. The compounds were tested in singlicate at one concentration ($10^{-7}$ M) in a total volume of 1000 µl. 980 µl of diluted membranes, 10 µl DMSO or unlabelled ligand, and 10 µl of [$^3$H]-8-OH-DPAT (0.6–0.7 nM) were incubated for 60 minutes at 27° C. The reaction was stopped by rapid filtration through Tomtec Cell Harvester (48 wells) using Filtermat B (presoaked in 0.1% PEI) filters. Filters were washed with ice-cold 50 mM Tris-HCl (pH 7.4) buffer (9×700 µl), dried, covered with MeltiLex B/HS scintillator sheets (Wallac) and heated at 80° C. to 90° C. for about 10 minutes, transferred into plastic sample bags (Wallac), sealed and put into 1024 Beta Plate scintillation counter (Wallac). Non-specific binding was determined in the presence of 5-HT ($10^{-5}$ M).

Data Analysis

The specific radioligand binding to the receptor was defined by the difference between total binding and non-specific binding, determined in the presence of an excess of unlabelled ligand. Results were expressed as percentage of control specific binding obtained in the presence of the compounds. The affinity values ($IC_{50}$) for the compounds were obtained by a nonlinear least squares regression analysis on the basis of a one binding site model.

$5\text{-HT}_{1A}$ Functional Assay (cAMP)

CHO/$5\text{-HT}_{1A}$ cells were random seeded at a density of about 200,000/well in 24 well plates the day prior to the experiment. On the day of the experiment, cells were pretreated for 15 minutes at 37° C. with 500 µM isobutyl-methylxantine (IBMX) dissolved in culture medium without serum. Wells were then divided in different groups in duplicate as follows: control, 10 µM FSK, 10 µM FSK+1 µM 5-HT as positive standard and 10 µM FSK+10 µM of the different compound under evaluation. Sample solutions were added and incubated for additional 15 minutes at 37° C. After incubation, medium was aspirated and the reaction stopped by adding 200 µl of lysis buffer. Plates were shaken for 5 minutes, then the lysate was removed and samples were stored at 4° C. until the day of the assay. For the cAMP evaluation, samples were properly diluted and the cAMP content was measured by an enzyme immunoassay system.

Data Analysis

Results are expressed as % inhibition of the cAMP accumulation induced by 10 µM FSK.

$D_4$ Radioligand Receptor Binding Assay

Membranes from CHO cells, expressing $D_4$ human receptors were suspended in incubation buffer.

Binding Assay

Binding assays were performed in MultiProbe 204 pipetting system (Packard), according to a predetermined mapping, consistent with the software Screen. The compounds were tested in singlicate at one concentration ($10^{-7}$ M) in a total volume of 1000 µl (980 µl of diluted membranes, 10 µl DMSO or unlabelled ligand, and 10 µl of [$^3$H] YM-09151-2 (0.15–0.25 nM). After incubation for 120 minutes at 27° C., the reaction was stopped by rapid filtration through Tomtec Cell Harvester (48 wells) using Filtermat B (presoaked in 0.1% PEI) filters. Filters were washed with ice-cold 50 mM Tris-HCl (pH 7.4) buffer (9×700 µl), dried, covered with MeltiLex B/HS (Wallac) scintillator sheets and heated in oven at 80° C.–90° C. for about 10 minutes, transferred into plastic sample bags (Wallac), sealed and put into 1024 Beta Plate scintillation counter (Wallac). Non-specific binding was determined in the presence of clozapine dissolved in DMSO to a final concentration of $10^{-5}$ M.

Data Analysis

The specific radioligand binding to the receptor was defined by the difference between total binding and non-specific binding, determined in the presence of an excess of unlabelled ligand. Results were expressed as percentage of control specific binding obtained in the presence of the compounds.

The following tables collect the biological data at the said receptors of the new compounds.

TABLE 4

% Inhibition at $5\text{-HT}_{1A}$ and D4 receptors

| Compound No. | $5HT_{1A}$ Receptor Binding Assay % Inhibition ($10^{-7}$ M) | $D_4$ Receptor Binding Assay % Inhibition ($10^{-7}$ M) |
|---|---|---|
| 1 | 80 | 60 |
| 4 | 73 | 36 |
| 5 | 91 | 69 |
| 9 | 96 | 54 |
| 10 | 76 | 57 |
| 18 | 70 | 58 |
| 22 | 81 | 77 |
| 26 | 94 | 49 |
| 27 | 87 | 70 |
| 35 | 88 | 59 |
| 39 | 91 | 72 |
| 43 | 94 | 54 |
| 44 | 94 | 69 |
| 52 | 90 | 47 |
| 56 | 92 | 65 |
| 60 | 88 | 30 |
| 61 | 90 | 44 |
| 69 | 90 | 41 |
| 71 | 71 | 43 |
| 72 | 92 | 41 |
| 73 | 87 | 51 |
| 77 | 75 | 36 |
| 78 | 86 | 40 |
| 86 | 92 | 52 |
| 87 | 77 | 58 |
| 89 | 92 | 34 |
| 90 | 98 | 79 |
| 91 | 84 | 39 |
| 92 | 88 | 54 |
| 95 | 92 | 46 |
| 103 | 81 | 50 |
| 106 | 92 | 37 |
| 107 | 96 | 69 |
| 111 | 94 | 32 |
| 112 | 87 | 43 |
| 120 | 98 | 49 |
| 123 | 98 | 57 |
| 124 | 99 | 49 |
| 125 | 90 | 51 |

TABLE 5

5-HT$_{1A}$ Affinity (IC$_{50}$) and Agonist Activity (cAMP % inhib.)

| Compound No. | 5-HT$_{1A}$ Receptor Binding IC$_{50}$ (nm) | cAMP % Inhibition |
|---|---|---|
| 9 | 4.8 | 80 |
| 26 | 6.6 | 68 |
| 27 | 6.4 | 44 |
| 35 | 15 | 66 |
| 39 | 9.8 | 63 |
| 43 | 1.2 | 73 |
| 44 | 2.5 | 47 |
| 52 | 16 | 54 |
| 56 | 11 | 65 |
| 60 | 1.8 | 71 |
| 61 | 5.2 | 26 |
| 69 | 13 | 52 |
| 78 | 18 | 27 |
| 89 | 10 | 66 |
| 90 | 4.6 | 62 |
| 92 | 15 | 46 |
| 94 | 0.96 | 75 |
| 95 | 7.3 | 22 |
| 106 | 7.4 | 68 |
| 107 | 5.3 | 54 |
| 111 | 4.4 | 68 |
| 112 | 13 | 9 |
| 120 | 6.0 | 17 |
| 123 | 1.2 | 63 |
| 124 | 11 | 47 |
| 125 | 3.3 | 49 |
| 126 | 15 | 44 |
| 128 | 8.4 | 61 |
| 129 | 5.5 | 13 |

We claim:

1. A method for treatment of anxiety disorders and affective disorders in a host in need of such treatment, which method comprises administering the host an effective amount of a compound of formula (I)

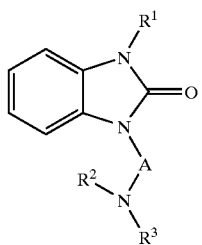

(I)

wherein:

$R^1$ is hydrogen or $C_1$–$C_6$-alkyl optionally substituted by $C_3$–$C_6$-cycloalkyl;

$R^2$ and $R^3$ together with the nitrogen form a saturated or unsaturated 5- or 6-membered heterocyclic ring optionally containing nitrogen or oxygen as an additional heteroatom, the heterocyclic ring thereof spiro-connected to another saturated or unsaturated heterocyclic group containing one or two heteroatoms selected from oxygen and nitrogen, the heterocyclic group being optionally mono- or di-substituted by a group selected from CF$_3$, $C_1$–$C_4$-alkyl, $C_1$–$C_4$-alkoxy, phenyl, benzyl, halogen, =O, and OH, or $R^2$ and $R^3$ together with the nitrogen form a saturated or unsaturated bi- or tricyclic heterocyclic ring system optionally containing nitrogen or oxygen as an additional heteroatom, the heterocyclic ring system is optionally substituted by a group selected from CF$_3$, $C_1$–$C_4$-alkyl, $C_1$–$C_4$-alkoxy, phenyl, benzyl, halogen, =O, and OH; and A is $C_2$–$C_4$-alkenylene, or a pharmaceutically acceptable salt thereof.

2. The method of claim 1, wherein in the compound of formula (I) or a pharmaceutically acceptable salt thereof:

$R^1$ is hydrogen or $C_1$–$C_6$-alkyl optionally substituted by $C_3$–$C_6$-cycloalkyl;

$R^2$ and $R^3$ together with the nitrogen form a 6-membered saturated or unsaturated heterocyclic ring optionally containing nitrogen as an additional heteroatom, wherein the heterocyclic ring is substituted by a group selected from phenyl, pyridinyl, pyrimidinyl, benzimidazolynyl, and phenyl mono- or di-substituted by a group selected from CF$_3$, CH$_3$, OCH$_3$, F, and Cl; and A is $C_2$–$C_4$-alkenylene, or a pharmaceutically acceptable salt thereof.

3. The method of claim 1, wherein in the compound of formula (I) or a pharmaceutically acceptable salt thereof:

$R^1$ is hydrogen or $C_1$–$C_4$-alkyl optionally substituted by cyclohexyl;

$R^2$ and $R^3$ together with the nitrogen form a 6-membered saturated or unsaturated heterocyclic ring optionally containing nitrogen as an additional heteroatom, wherein the heterocyclic ring is substituted by a group selected from pyridyl, pyrimidinyl, phenyl, and phenyl mono- or di-substituted by a group selected from CF$_3$, CH$_3$, OCH$_3$, F, and Cl; and A butenylene.

4. The method of claim 1, wherein in the compound of formula (I) or a pharmaceutically acceptable salt thereof:

$R^1$ is hydrogen, methyl, ethyl, n-propyl, or cyclohexylmethyl;

$R^2$ and $R^3$ together with the nitrogen form a ring selected from the group consisting of piperazine, piperidine, and tetrahydropyridine, each substituted by a group selected from pyridyl, pyrimidinyl, phenyl, and phenyl mono- or di-substituted by a group selected from CF$_3$, CH$_3$, and Cl; and A is butenylene.

5. The method of claim 1, wherein in the compound of formula (I) or a pharmaceutically acceptable salt thereof:

$R^1$ is hydrogen, methyl, n-propyl, or cyclohexylmethyl;

$R^2$ and $R^3$ together with the nitrogen form a piperazine ring substituted by a group selected from trifluoromethylphenyl, chlorophenyl, pyridyl, and pyrimidinyl; and A is butenylene.

6. The method of claim 1, wherein in the compound of formula (I) or a pharmaceutically acceptable salt thereof: A is $C_2$–$C_4$-alkenylene.

7. The method of claim 1, wherein the compound of formula (I) or a pharmaceutically acceptable salt thereof is

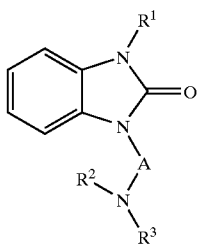
(I)

wherein:
$R^1$ is hydrogen, methyl, n-propyl, or cyclohexylmethyl;
$R^2$ and $R^3$ together with the nitrogen form a piperazine ring substituted by a group selected from trifluoromethylphenyl, chlorophenyl, pyridyl, and pyrimidinyl: and
A is butenylene,
or a pharmaceutically acceptable salt thereof.

8. The method of claim 1, wherein the compound of formula (I) or a pharmaceutically acceptable salt thereof is selected from the group consisting of;

(a) 1-methyl-3-(4-{4-[3-(trifluoromethyl)phenyl] piperazin-1-yl}-(2Z)-butenyl)-1,3-dihydro-2H-benzimidazol-2-one;

(b) 1-n-propyl-3-(4-{4-[3-(trifluoromethyl)phenyl] piperazin-1-yl}-(2Z)-butenyl)-1,3-dihydro-2H-benzimidazol-2-one;

(c) 1-methyl-3-(4-{4-[3-(trifluoromethyl)phenyl] piperazin-1-yl}-(2E)-butenyl)-1,3-dihydro-2H-benzimidazol-2-one; and (d) 1-cyclohexylmethyl-3-(4-{4-[2-pyridyl]piperazin-1-yl}-(2E)-butenyl)-1,3-dihydro-2H-benzimidazol-2-one, or a pharmaceutically acceptable salt thereof.

* * * * *